United States Patent [19]

Khartchenko et al.

[11] Patent Number: 5,464,608
[45] Date of Patent: Nov. 7, 1995

[54] COMPOSITION FOR THE CLEANING OF TEETH AND THE PROPHYLAXIS OF CARIES

[75] Inventors: Serguei V. Khartchenko; Nadejda Khartchenko; Alina Khartchenko; Alissa S. Khartchenko, all of Alberta, Canada

[73] Assignee: Regents of the University of Minnesota, Minneapolis, Minn.

[21] Appl. No.: 141,667

[22] Filed: Oct. 26, 1993

[51] Int. Cl.$^6$ .............................. A61K 7/16; A61K 7/20; A61K 9/46; A61K 9/20
[52] U.S. Cl. .................. 424/53; 424/44; 424/49; 424/464; 424/441
[58] Field of Search ..................... 424/44, 49–58

[56] References Cited

U.S. PATENT DOCUMENTS

| | | | |
|---|---|---|---|
| 2,470,906 | 5/1949 | Taylor | 167/93 |
| 3,065,139 | 11/1962 | Ericsson et al. | 167/72 |
| 3,772,431 | 11/1973 | Mlkvy et al. | 424/44 |
| 3,886,265 | 5/1975 | Evers et al. | 424/44 |
| 3,888,976 | 6/1975 | Mlkvy et al. | 424/44 |
| 4,115,293 | 9/1978 | Schoenholz et al. | 252/102 |
| 4,971,782 | 11/1990 | Rudy et al. | 424/53 |
| 5,223,264 | 6/1993 | Wehling et al. | 424/466 |

*Primary Examiner*—Shep K. Rose
*Attorney, Agent, or Firm*—Schwegman, Lundberg & Woessner

[57] ABSTRACT

The composition presents itself in the form of rapidly dissolving water soluble tablets, which contain multivitamins, sodium percarbonate, sodium bicarbonate, citric acid, various food flavors and food dyes. These components are mixed in such percentage and weight proportions, that when placed in contact with human saliva, a pH of 5.4–5.6 is created within the oral cavity. A concurrent excretion of carbon dioxide ($CO_2$) and oxygen (O) occurs. Both of these reactions enhance the desired effect, of cleaning both soft and hard tartar from the teeth, while at the same time diminishing not only the amount of pathogenic microflora, but also the inflammatory processes in the gum and mucus membrane. The end result is a significant prophylaxis of caries, achieved without any harm being done to the enamel of the teeth.

The novel effect of the invention becomes apparent in that the offered composition can be utilized in either of two forms. Firstly, the tablets may be ingested and dissolved directly within the oral cavity; or, and secondly, the same tablet may be dissolved in 150–200 ml. of drinking water and then ingested. A more pronounced prophylaxis occurs with the joint use of the tablet and mouth wash, one after the other.

The use of the offered substance for the cleaning of teeth and the prophylaxis of caries is complemented by its use as a breath freshener and deodorizer.

6 Claims, 6 Drawing Sheets

Fig. 2A

| (a) Effectiveness of the influence in %. Two years of use (examination of 4 groups of 250 people) | | (b) During the use of the offered composition in % | (c) Toothpaste - by brush with fluoride additives | (d) Mouthwash - with fluoride additives such as "Cepacol" | 1 pH | 2 Citric acid | 3 Water soluble poly-vitamins | 4 Sodium bicarbonate | 5 Food flavor | 6 Food dyes | 7 Sodium percarbonate | 8 Comments |
|---|---|---|---|---|---|---|---|---|---|---|---|---|
| 1 Freshening and deodorizing effect | Pleasant feeling. Freshness and good breath | 55 | | | 5.0 | 68 | 1.7 | 22 | 7.2 | 0.1 | 1.0 | |
| | | 60 | | | 5.2 | 66 | 1.5 | 24 | 7.3 | 0.2 | 1.0 | |
| | | 83 | | | 5.4 | 64 | 0.9 | 26 | 7.8 | 0.3 | 1.0 | |
| | | 90 | 95 | 47 | 5.5 | 62 | 0.6 | 28 | 7.9 | 0.5 | 1.0 | |
| | | 97 | | | 5.6 | 60 | 0.5 | 30 | 8.0 | 0.5 | 1.0 | |
| | | 20 | | | 5.8 | 58 | 0.2 | 32 | 8.2 | 0.6 | 1.0 | |
| | Unpleasant feeling. Burning of the tongue. Aching gums. Absence of freshness | 45 | | | 5.0 | 68 | 1.7 | 22 | 7.2 | 0.1 | 1.0 | |
| | | 40 | | | 5.2 | 66 | 1.5 | 24 | 7.3 | 0.2 | 1.0 | |
| | | 17 | | | 5.4 | 64 | 0.9 | 26 | 7.8 | 0.3 | 1.0 | |
| | | 10 | 5 | 63 | 5.5 | 62 | 0.6 | 28 | 7.9 | 0.5 | 1.0 | |
| | | 3 | | | 5.6 | 60 | 0.5 | 30 | 8.0 | 0.5 | 1.0 | |
| | | 80 | | | 5.8 | 58 | 0.2 | 32 | 8.2 | 0.6 | 1.0 | |
| 2 Removal of soft plaque and tartar | During sucking of the tablet - "candy" | 90 | | | 5.0 | 68 | 1.7 | 22 | 7.2 | 0.1 | 1.0 | Increase in solubility of enamel |
| | | 89 | | | 5.2 | 66 | 1.5 | 24 | 7.3 | 0.2 | 1.0 | |
| | | 86 | | | 5.4 | 64 | 0.9 | 26 | 7.8 | 0.3 | 1.0 | |
| | | 87 | 60 | 10 | 5.5 | 62 | 0.6 | 28 | 7.9 | 0.5 | 1.0 | |
| | | 87 | | | 5.6 | 60 | 0.5 | 30 | 8.0 | 0.5 | 1.0 | |
| | | 30 | | | 5.8 | 58 | 0.2 | 32 | 8.2 | 0.6 | 1.0 | |
| | During use of the mouthwash | 73 | | | 5.0 | 68 | 1.7 | 22 | 7.2 | 0.1 | 1.0 | Sour taste |
| | | 71 | | | 5.2 | 66 | 1.5 | 24 | 7.3 | 0.2 | 1.0 | |
| | | 70 | | | 5.4 | 64 | 0.9 | 26 | 7.8 | 0.3 | 1.0 | |
| | | 63 | | | 5.5 | 62 | 0.6 | 28 | 7.9 | 0.5 | 1.0 | |
| | | 60 | | | 5.6 | 60 | 0.5 | 30 | 8.0 | 0.5 | 1.0 | |
| | | 25 | | | 5.8 | 58 | 0.2 | 32 | 8.2 | 0.6 | 1.0 | |

Fig. 2B

| (a) Effectiveness of the influence in %. Two years of use (examination of 4 groups of 250 people) | | (b) During the use of the offered composition in % | (c) Toothpaste - by brush with fluoride additives | (d) Mouthwash - with fluoride additives such as "Cepacol" | 1 pH | 2 Citric acid | 3 Water soluble poly-vitamins | 4 Sodium bicar-bonate | 5 Food flavor | 6 Food dyes | 7 Sodium percar-bonate | 8 Comments |
|---|---|---|---|---|---|---|---|---|---|---|---|---|
| 3 Removal of hard plaque tartar and staining caused by smoking | During sucking of the tablet - "candy" | 97 | | | 5.0 | 68 | 1.7 | 22 | 7.2 | 0.1 | 1.0 | Acidic sensation |
| | | 92 | 10 - 15 | | 5.2 | 66 | 1.5 | 24 | 7.3 | 0.2 | 1.0 | |
| | | 90 | | | 5.4 | 64 | 0.9 | 26 | 7.8 | 0.3 | 1.0 | |
| | | 83 | | | 5.5 | 62 | 0.6 | 28 | 7.9 | 0.5 | 1.0 | |
| | | 80 | | | 5.6 | 60 | 0.5 | 30 | 8.0 | 0.5 | 1.0 | |
| | | 20 | | | 5.8 | 58 | 0.2 | 32 | 8.2 | 0.6 | 1.0 | |
| | During use of the mouthwash | 66 | | | 5.0 | 68 | 1.7 | 22 | 7.2 | 0.1 | 1.0 | |
| | | 65 | | | 5.2 | 66 | 1.5 | 24 | 7.3 | 0.2 | 1.0 | |
| | | 60 | | | 5.4 | 64 | 0.9 | 26 | 7.8 | 0.3 | 1.0 | |
| | | 54 | | | 5.5 | 62 | 0.6 | 28 | 7.9 | 0.5 | 1.0 | |
| | | 52 | | | 5.6 | 60 | 0.5 | 30 | 8.0 | 0.5 | 1.0 | |
| | | 10 | | | 5.8 | 58 | 0.2 | 32 | 8.2 | 0.6 | 1.0 | |
| 4 Removal of soft and hard tartar and plaque during the combined use of both tablet and mouthwash | | 100 | | | 5.0 | 68 | 1.7 | 22 | 7.2 | 0.1 | 1.0 | |
| | | 96 | | | 5.2 | 66 | 1.5 | 24 | 7.3 | 0.2 | 1.0 | |
| | | 93 | | | 5.4 | 64 | 0.9 | 26 | 7.8 | 0.3 | 1.0 | |
| | | 90 | | | 5.5 | 62 | 0.6 | 28 | 7.9 | 0.5 | 1.0 | |
| | | 89 | | | 5.6 | 60 | 0.5 | 30 | 8.0 | 0.5 | 1.0 | |
| | | 45 | | | 5.8 | 58 | 0.2 | 32 | 8.2 | 0.6 | 1.0 | |

Fig. 2C

| (a) Effectiveness of the influence in %. Two years of use (examination of 4 groups of 250 people) | | (b) During the use of the offered composition in % | (c) Toothpaste - by brush with fluoride additives | (d) Mouthwash - with fluoride additives such as "Cepacol" | 1 pH | 2 Citric acid | 3 Water soluble poly-vitamins | 4 Sodium bicarbonate | 5 Food flavor | 6 Food dyes | 7 Sodium percarbonate | 8 Comments |
|---|---|---|---|---|---|---|---|---|---|---|---|---|
| 5 Whitening effect | During use of the tablet - "candy" | 97 | | | 5.0 | 68 | 1.7 | 22 | 7.2 | 0.1 | 1.0 | Acidic sensation |
| | | 92 | | | 5.2 | 66 | 1.5 | 24 | 7.3 | 0.2 | 1.0 | |
| | | 90 | | | 5.4 | 64 | 0.9 | 26 | 7.8 | 0.3 | 1.0 | |
| | | 83 | | | 5.5 | 62 | 0.6 | 28 | 7.9 | 0.5 | 1.0 | |
| | | 80 | | | 5.6 | 60 | 0.5 | 30 | 8.0 | 0.5 | 1.0 | |
| | | 20 | | | 5.8 | 58 | 0.2 | 32 | 8.2 | 0.6 | 1.0 | |
| | During use of the mouthwash | 66 | | | 5.0 | 68 | 1.7 | 22 | 7.2 | 0.1 | 1.0 | |
| | | 65 | | | 5.2 | 66 | 1.5 | 24 | 7.3 | 0.2 | 1.0 | |
| | | 60 | | | 5.4 | 64 | 0.9 | 26 | 7.8 | 0.3 | 1.0 | |
| | | 54 | | | 5.5 | 62 | 0.6 | 28 | 7.9 | 0.5 | 1.0 | |
| | | 52 | | | 5.6 | 60 | 0.5 | 30 | 8.0 | 0.5 | 1.0 | |
| | | 10 | | | 5.8 | 58 | 0.2 | 32 | 8.2 | 0.6 | 1.0 | |
| | During use of both the tablets and the mouthwash | 100 | | | 5.0 | 68 | 1.7 | 22 | 7.2 | 0.1 | 1.0 | |
| | | 96 | | | 5.2 | 66 | 1.5 | 24 | 7.3 | 0.2 | 1.0 | |
| | | 93 | | | 5.4 | 64 | 0.9 | 26 | 7.8 | 0.3 | 1.0 | |
| | | 90 | | | 5.5 | 62 | 0.6 | 28 | 7.9 | 0.5 | 1.0 | |
| | | 89 | | | 5.6 | 60 | 0.5 | 30 | 8.0 | 0.5 | 1.0 | |
| | | 45 | | | 5.8 | 58 | 0.2 | 32 | 8.2 | 0.6 | 1.0 | |

Fig. 2D

| (a) Effectiveness of the influence in %. Two years of use (examination of 4 groups of 250 people) | | (b) During the use of the offered composition in % | (c) Toothpaste - by brush with fluoride additives | (d) Mouthwash - with fluoride additives such as "Cepacol" | 1 pH | 2 Citric acid | 3 Water soluble poly-vitamins | 4 Sodium bicar-bonate | 5 Food flavor | 6 Food dyes | 7 Sodium percar-bonate | 8 Comments |
|---|---|---|---|---|---|---|---|---|---|---|---|---|
| 6 Carries prophylactic effect | During use of the tablet - "candy" | 60 | | | 5.4 | 64 | 0.9 | 26 | 7.8 | 0.3 | 1.0 | Indicated are optimal correlation and pH for which best effect was observed |
| | | 65 | | | 5.6 | 60 | 0.5 | 30 | 8.0 | 0.5 | 1.0 | |
| | During use of the mouthwash | 49 | 35 | 10 - 15 | 5.4 | 64 | 0.9 | 26 | 7.8 | 0.3 | 1.0 | |
| | | 53 | | | 5.6 | 60 | 0.5 | 30 | 8.0 | 0.5 | 1.0 | |
| | During use of both the tablets and mouthwash | 78 | | | 5.4 | 64 | 0.5 | 30 | 8.0 | 0.5 | 1.0 | |
| | | 80 | | | 5.5 | 62 | 0.6 | 28 | 7.9 | 0.5 | 1.0 | |
| | | 81 | | | 5.6 | 60 | 0.5 | 30 | 8.0 | 0.5 | 1.0 | |
| 7 Reduction in microflora | After use of the tablets - "candy" | 75 | | | 5.0 | 68 | 1.7 | 22 | 7.2 | 0.1 | 1.0 | |
| | | 73 | | | 5.2 | 66 | 1.5 | 24 | 7.3 | 0.2 | 1.0 | |
| | | 71 | | | 5.4 | 64 | 0.9 | 26 | 7.8 | 0.3 | 1.0 | |
| | | 70 | | | 5.5 | 62 | 0.6 | 28 | 7.9 | 0.5 | 1.0 | |
| | | 89 | | | 5.6 | 60 | 0.5 | 30 | 8.0 | 0.5 | 1.0 | |
| | | 57 | | | 5.8 | 58 | 0.2 | 32 | 8.2 | 0.6 | 1.0 | |
| | After use of both the tablets and the mouthwash | 81 | | | 5.0 | 68 | 1.7 | 22 | 7.2 | 0.1 | 1.0 | |
| | | 81 | 65 - 70 | 56 - 69 | 5.2 | 66 | 1.5 | 24 | 7.3 | 0.2 | 1.0 | |
| | | 80 | | | 5.4 | 64 | 0.9 | 26 | 7.8 | 0.3 | 1.0 | |
| | | 77 | | | 5.5 | 62 | 0.6 | 28 | 7.9 | 0.5 | 1.0 | |
| | | 75 | | | 5.6 | 60 | 0.5 | 30 | 8.0 | 0.5 | 1.0 | |
| | | 56 | | | 5.8 | 58 | 0.2 | 32 | 8.2 | 0.6 | 1.0 | |

Fig. 2E

| (a) Effectiveness of the influence in %. Two years of use (examination of 4 groups of 250 people) | | (b) During the use of the offered composition in % | (c) Toothpaste - by brush with fluoride additives | (d) Mouthwash - with fluoride additives such as "Cepacol" | 1 pH | 2 Citric acid | 3 Water soluble polyvitamins | 4 Sodium bicarbonate | 5 Food flavor | 6 Food dyes | 7 Sodium percarbonate | 8 Comments |
|---|---|---|---|---|---|---|---|---|---|---|---|---|
| 8 Reduction in bleeding of gums | After use of the tablets - "candy" | 45 | 30 - 40 | 15 - 20 | 5.0 | 68 | 1.7 | 22 | 7.2 | 0.1 | 1.0 | |
| | | 57 | | | 5.2 | 66 | 1.5 | 24 | 7.3 | 0.2 | 1.0 | |
| | | 65 | | | 5.4 | 64 | 0.9 | 26 | 7.8 | 0.3 | 1.0 | |
| | | 64 | | | 5.5 | 62 | 0.6 | 28 | 7.9 | 0.5 | 1.0 | |
| | | 64 | | | 5.6 | 60 | 0.5 | 30 | 8.0 | 0.5 | 1.0 | |
| | | 63 | | | 5.8 | 58 | 0.2 | 32 | 8.2 | 0.6 | 1.0 | |
| | After use of both the tablets and the mouthwash | 49 | | | 5.0 | 68 | 1.7 | 22 | 7.2 | 0.1 | 1.0 | |
| | | 60 | | | 5.2 | 66 | 1.5 | 24 | 7.3 | 0.2 | 1.0 | |
| | | 70 | | | 5.4 | 64 | 0.9 | 26 | 7.8 | 0.3 | 1.0 | |
| | | 79 | | | 5.5 | 62 | 0.6 | 28 | 7.9 | 0.5 | 1.0 | |
| | | 64 | | | 5.6 | 60 | 0.5 | 30 | 8.0 | 0.5 | 1.0 | |
| | | 63 | | | 5.8 | 58 | 0.2 | 32 | 8.2 | 0.6 | 1.0 | |
| 9 Anti-inflammatory effect | After use of the tablets - "candy" | 66 | 25 - 30 | 10 - 15 | 5.0 | 68 | 1.7 | 22 | 7.2 | 0.1 | 1.0 | |
| | | 63 | | | 5.2 | 66 | 1.5 | 24 | 7.3 | 0.2 | 1.0 | |
| | | 60 | | | 5.4 | 64 | 0.9 | 26 | 7.8 | 0.3 | 1.0 | |
| | | 59 | | | 5.5 | 62 | 0.6 | 28 | 7.9 | 0.5 | 1.0 | |
| | | 59 | | | 5.6 | 60 | 0.5 | 30 | 8.0 | 0.5 | 1.0 | |
| | | 57 | | | 5.8 | 58 | 0.2 | 32 | 8.2 | 0.6 | 1.0 | |
| | After use of both the tablets and the mouthwash | 67 | | | 5.0 | 68 | 1.7 | 22 | 7.2 | 0.1 | 1.0 | |
| | | 63 | | | 5.2 | 66 | 1.5 | 24 | 7.3 | 0.2 | 1.0 | |
| | | 64 | | | 5.4 | 64 | 0.9 | 26 | 7.8 | 0.3 | 1.0 | |
| | | 64 | | | 5.5 | 62 | 0.6 | 28 | 7.9 | 0.5 | 1.0 | |
| | | 60 | | | 5.6 | 60 | 0.5 | 30 | 8.0 | 0.5 | 1.0 | |
| | | 60 | | | 5.8 | 58 | 0.2 | 32 | 8.2 | 0.6 | 1.0 | |

COMPOSITION FOR THE CLEANING OF TEETH AND THE PROPHYLAXIS OF CARIES

FIELD OF THE INVENTION

The invention is a composition for the cleaning of teeth and the prophylaxis of caries, by removal of both soft and hard tartar from the teeth, while at the same time diminishing not only the amount of pathogenic microflora, but also the inflammatory processes in the gums and mucus membrane all without any harm being done to the enamel of the teeth. This use is complemented by use of the composition as a breath freshener and breath deodorizer.

BACKGROUND

At the present time a series of prophylactic substances are known, which are intended to address either the cleaning of teeth and the prevention of caries, or the freshening and deodorizing of breath. Few exist which attempt to solve both problems simultaneously, and those that do invariably involve the use of flouride.

For example, a whole series of caries prophylactic substances are known, which in composition contain either fluoride or its derivatives. Fluoride creates a good caries-static effect, but its use involves certain health risks, the consequences of which are only just becoming known. Flouride is a biostimulator and an known carcinogen. Its use is especially dangerous during the presence of inflammatory occurrences in the mucus membrane of the oral cavity and gums. In fact, iontophoresis of fluoride during the inflammatory occurrences in gums is prohibited.

Tooth pastes with flourides, are inefficient, since the tartar, especially the hard tartar, remains in the spaces between the teeth and serves as a wonderful depot for the pathogenic microflora. Metabolites of this microflora lead to development of caries and inflammatory occurrences in the gums. Most of all, the use of tooth brushes has its own negative effect, in that during their frequent and correct use, tooth enamel rubs off and wedge-formed defects are created.

Tablets or candies, which are used for the deodorizing and freshening of the oral cavity, are already known. However, these tablets do not remove tartar. Analogous tablets, which are intended for this goal, may be hazardous. This second case occurs when tablets containing menthol cause vessel spasms of the mucous membrane of the oral cavity. This may sometimes lead to reflex spasms of the brain vessels, since menthol possesses an emphasized vessel thinning influence. Finally, substitutes of natural sugars, which are often used in these products, may have carcinogenic properties.

A prototype which is similar to the offered invention is (international claim NO 81/02102, Australia —contains sodium bicarbonate 15%, citric acid 80%, dyes 4%, flavor 1%). However, this composition, possesses a series of substantial deficiencies, particularly, very sour pH (4.5–4.9), at which levels the enamel of teeth will dissolve. Such levels are inadequate for the prophylaxis of caries, and instead increase the likelihood of their occurrence. This substance does not contain in its composition any substances which are capable of developing oxygen (O) during their contact with the saliva and bacterial cells. When special bacteria-static or bactericidal substances are introduced, they imbalance the symbiosis, of the microflora of the oral cavity.

SUMMARY OF THE INVENTION

The aim of this invention is the creation of a substance, which allows for a simultaneously increase in the efficient removal of tartar, without harming the enamel of the teeth or the body as a whole, while at the same time decreasing the quantity of the pathogenic microflora, and creating in the oral cavity conditions, which allow for the prophylaxis of the caries.

The aim is achieved in that a mix of the following substances in the following proportions, by weight, is made: 60 to 64% citric acid; 26 to 30% sodium bicarbonate; about 1% sodium percarbonate; and 0.5 to 0.9% water soluble vitamins including ascorbic acid. The water soluble vitamins also preferably include vitamin B.

This mix, once in contact with saliva, enters into a reaction with the water contained in the saliva said reaction excretes carbon dioxide ($CO_2$) and oxygen (O) due to the reaction of the vitamins and sodium percarbonate with the saliva which gases recombine with the saliva to loosen the tartar and wash out microflora from the gum pockets. The water soluble vitamins and sodium percarbonate during the contact with the mucous of the saliva and bacterial cells provokes a chemical reaction in which oxygen (O) is excreted, the bactericidal influence of which is widely known. The mix during contact with saliva, creates in the oral cavity a pH of 5.4–5.6. This pH, as many experiments have shown, is optimal, since it realizes an excellent removal of the tartar, while at the same time not harming the enamel of teeth. It is widely known that the tartar is an excellent depot for microflora, which are the instigators of caries and inflammatory processes. This is why, an efficient removal of the tartar, leads to a good caries prophylactic effect. The development of carbon dioxide ($CO_2$) and oxygen (O) in conjunction with a complete set of flavors and dyes, leads to an excellent deodorizing effect and freshening of the oral cavity.

Cleaning of the gum pocket, mucous membrane and teeth from excessive mucous and tartar, allows the water soluble vitamins to simultaneously influence a positive reaction on the gum vessels and mucous membrane thereby improving the metabolism in the tissues of the oral cavity. It is very important that all of these reactions in the oral cavity take place within the range pH 5.4–5.6. If the acidity of the mix (offered composition & saliva) is increased, then this leads to a greater solubility (loss) of the enamel. On the contrary, if the pH is greater than 5.6, then the effectiveness of cleaning will sharply decrease.

BRIEF DESCRIPTION OF THE DRAWINGS

FIG. 2A illustrates empirical test results of various compositions in chart form.

FIG. 2B illustrates empirical test results of various compositions in chart form.

FIG. 2C illustrates empirical test results of various compositions in chart form.

DETAILED DESCRIPTION OF PREFERRED EMBODIMENTS

Figure 1:
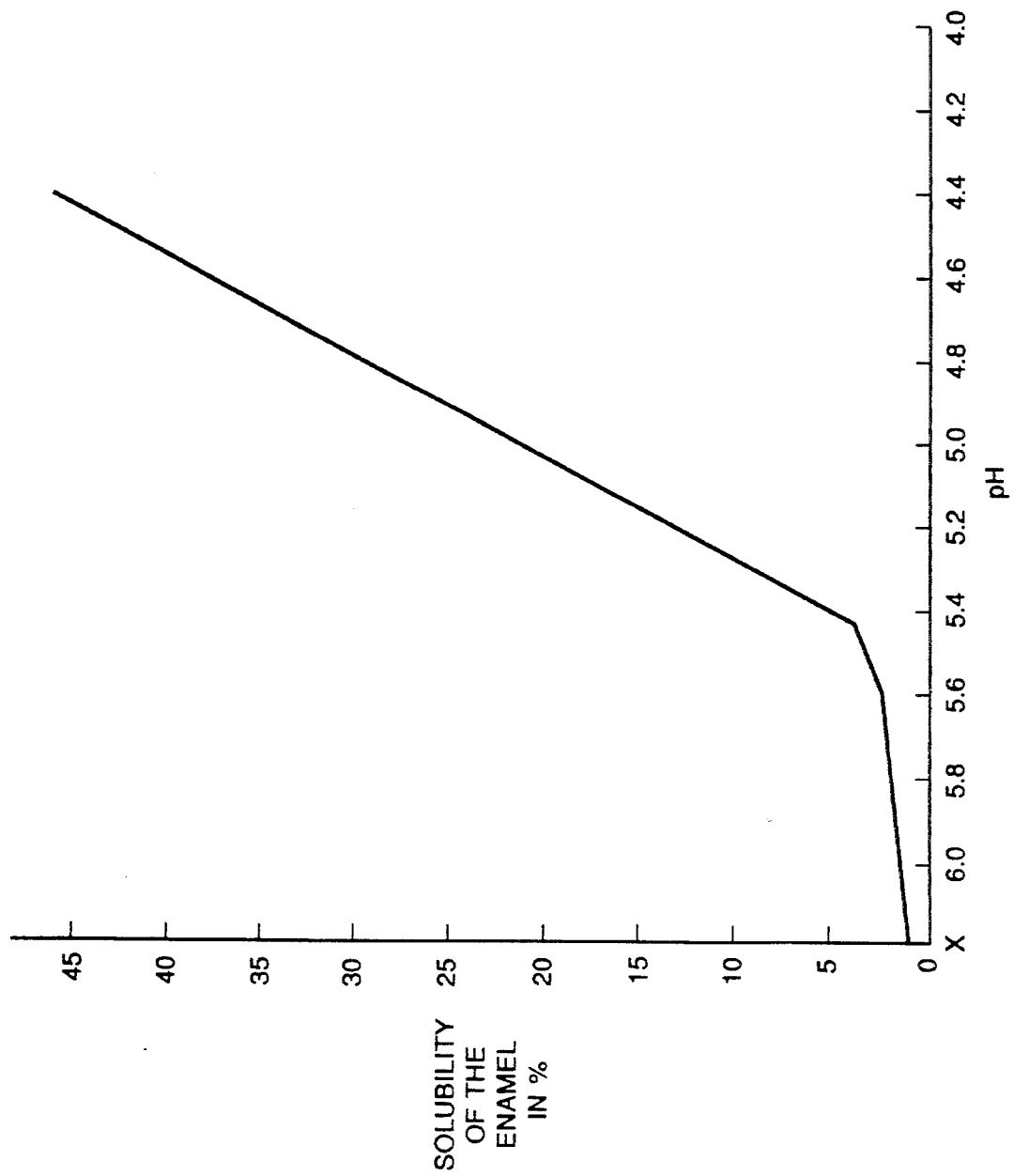
FIG. 1 illustrates the relationship between pH levels and solubility of the enamel.

The composition is mixed from the following components in the following proportions: Citric acid 60–64 %, water soluble multi-vitamins 0.5–0.9%, sodium bicarbonate 26–30%, food flavors 7.8–8.0 %, food dyes 0.3–0.5%, sodium percarbonate 1.0–1.0%.

This mix is granulated and compacted in a mould to form a tablet. The tablet may be used in either or both of two ways. First, the tablet may be placed directly into the mouth. As soon as it makes a contact with the saliva, it will begin dissolving with the resultant chemically reactive processes discussed earlier. This use, in the form of a tablet or "Candy" is very effective for the removal of hard and soft tartar and also for the pigmentation of the teeth occasioned by smoking etc.. Moving the tablet with the tongue on the surface of the teeth, will yield the desired cleaning effect. Second, a tablet may be dissolved in a glass of potable water and then used as a mouth wash. A single tablet or "Candy", is placed in 150–200 ml of drinking water. It will completely dissolve in a period of 30–60 seconds.

The above described multiple methods of use makes the offered substance very convenient, in that it can be used in any conditions (at home, at work, in transport, in the restaurant, in school, and so on).

The optimal effectiveness of the offered mix, occurs when its components are mixed in the following proportions: citric acid, water soluble vitamins including vitamin C and, preferably, vitamin B, sodium bicarbonate, food flavors, and food dyes, sodium respectively: 60–64%, 0.5–0.9%, 26to 30%, 7.8.to 8.0%, 0.3to 0.5%, about 1.0%.

Particularly, the indicated components mixed in the indicated proportions will, when mixed with saliva, result in an oral acidity level within the desirable pH 5.4–5.6 range, thereby maximizing the cleaning of the teeth from soft and hard tartar, while at the same time reducing the quantity pathogenic microflora, whitening of the teeth from discoloration, reducing the bleeding of the gums, reducing inflammatory occurrences and achieving a sense of freshness and pleasant breath all without causing any harm to the enamel of the teeth and body as a whole. (See FIGS. 2A, 2B, 2C, 2D and 2E).

The following is observable from the Chart which is FIGS. 2A, 2B, 2C, 2D and 2E.

Enamel solubility sharply increases, as pH levels decrease below 5.4. This means that a more acidic pH gives rise to an increased hazard to enamel. Conversely, an increase of alkalinity so as to increase the pH level beyond 5.6, diminishes the effectiveness of the influence of the composition.

The results of use of the offered composition in both tablet and mouthwash form, used separately and jointly indicates:

1. The prophylaxis of caries is significantly more efficaciously achieved, than by usage of conventional prophylactic substances.
2. The ease of use of the offered substance is such that it can be used in practically any circumstances.
3. In combinative usage as tablet and mouthwash, it is possible to achieve not only a sum of effects, but also an improvement to the metabolism of the tissue in the oral cavity. Removal of hard and soft plaque and tartar from the teeth, with a concurrent reduction in the quantity of pathogenic microflora, contribute to the caries prophylactic effect all occur without the use of active chemical biological stimulators such as fluoride.

We claim:

1. A granulated carbon dioxide and oxygen evolving tablet or candy composition for the cleaning of teeth and the prophylaxis of caries, by removal of both soft and hard tartar from the teeth along with pathogenic microflora, and the diminution of the inflammatory processes present in the gums and mucus membrane without harm to the enamel of the teeth, said composition consisting essentially of the following in the indicated proportionate percentages, by weight, citric acid 60–64%, 0.5–0.9% ascorbic acid and other water soluble vitamins, sodium bicarbonate 26–30%, and sodium percarbonate about 1%, whereby said composition, when contacted with saliva, creates a pH level of 5.4 to 5.6 and evolves carbon dioxide and oxygen effective to deodorize and freshen the oral cavity.

2. The composition of claim 1 wherein said water soluble vitamins include vitamin B.

3. The composition of claim 2 including food flavours in the by weight proportionate percentage of 7.8 to 8.0%.

4. The composition of claim 3 including food dyes in the by weight proportionate percentage of 0.3 to 0.5%.

5. A molded tablet consisting of a granulated carbon dioxide and oxygen evolving composition for the cleaning of teeth and the prophylaxis of caries, by removal of soft and hard tartar from the teeth along with pathogenic microflora and for the diminution of inflammatory processes present in the gums and mucus membrane without harm to the enamel of the teeth consisting essentially of, by weight:

60 to 64% citric acid;

26 to 30% sodium bicarbonate;

about 1% sodium percarbonate; and 0.5 to 0.9% ascorbic acid and other water soluble vitamins, whereby said tablet, when placed in the oral cavity, reacts with the water in saliva to create an oral cavity pH level of 5.4 to 5.6 and evolves carbon dioxide and oxygen effective to deodorize and freshen the oral cavity.

6. The tablet of claim 5 wherein said vitamins include vitamin B.

* * * * *